United States Patent [19]
Ishii et al.

[11] Patent Number: 5,650,304
[45] Date of Patent: Jul. 22, 1997

[54] PROCESS FOR PRODUCING L-LYSINE BY FERMENTATION

[75] Inventors: Toshimasa Ishii; Manabu Yokomori; Harufumi Miwa, all of Kawasaki, Japan

[73] Assignee: Ajinomoto Co., Inc., Tokyo, Japan

[21] Appl. No.: 383,651

[22] Filed: Feb. 3, 1995

Related U.S. Application Data

[63] Continuation of Ser. No. 178,452, Jan. 5, 1994, abandoned, which is a continuation of Ser. No. 739,436, Aug. 2, 1991, abandoned.

[30] Foreign Application Priority Data

Aug. 3, 1990 [JP] Japan ..................... 2-206498

[51] Int. Cl.$^6$ ..................... C12P 13/08
[52] U.S. Cl. ..................... 435/115; 435/840; 435/843
[58] Field of Search ..................... 435/115

[56] References Cited

U.S. PATENT DOCUMENTS

| | | | |
|---|---|---|---|
| 4,066,501 | 1/1978 | Tosaka et al. | 435/115 |
| 4,861,722 | 8/1989 | Sano et al. | 435/115 |
| 4,954,441 | 9/1990 | Katsumata et al. | 435/115 |
| 5,196,326 | 3/1993 | Kuronuma et al. | |

FOREIGN PATENT DOCUMENTS 2050080  3/1971  France.

OTHER PUBLICATIONS

U.S. application No. 08/178,552, filed Jan. 5, 1994.

U.S. application No. 07/986,749, filed Dec. 8, 1992.

*Primary Examiner*—Herbert J. Lilling
*Attorney, Agent, or Firm*—Oblon, Spivak, McClelland, Maier & Neustadt, P.C.

[57] ABSTRACT

The present invention relates to (a) process for producing L-lysine by fermentation which comprises culturing a microorganism having resistance to 4-N-(D-alanyl)-2,4-diamino-2,4-dideoxy-L-arabinose 2,4-dideoxy-L-arabinose or a derivative thereof and belonging to the genus Brevibacterium or the genus Corynebacterium, (b) said bacterium therefore and (c) a method of producing said bacterium.

10 Claims, No Drawings

PROCESS FOR PRODUCING L-LYSINE BY FERMENTATION

This application is a continuation of application Ser. No. 08/178,452, filed on Jan. 5, 1994, which is a continuation of application Ser. No. 07/739,436, filed on Aug. 2, 1991, both now abandoned.

BACKGROUND OF THE INVENTION

1. Field of the Invention

The present invention relates to a process for producing L-lysine by fermentation. L-lysine is one of the twenty naturally occurring essential amino acids. In addition to other uses, L-lysine is useful in livestock production. Since cereals, which are common livestock (e.g. broilers and pigs) feed, do not contain sufficient levels of the amino acid for the livestock's nutritional requirements it is necessary to supplement the feed with L-lysine. Thus it is necessary to develop an efficient method for L-lysine production.

2. Description of the Prior Art

In previously described processes for the microbial production of L-lysine by fermentation, specific lysine producing microorganisms have been isolated or derived from naturally occurring lysine producers. Most of these artificially selected mutants are derived from microorganisms belonging to the genus Brevibacterium or alternatively the genus Corynebacterium. In both of these genus, L-lysine production is achieved by potentiating the L-lysine biosynthesis system by a combination or sequential ligation of properties such as auxotrophy, sensitivity, analog resistance, etc. (Tosaka, Takinami in "Fermentation of Amino Acid", edited by Aida, Takinami, Chibata, Nakayama and Yamada, Gakkai Publishing Center, 1986, page 273 ff). These methods have limited ability to select organisms which produce L-lysine at increased levels. It is therefore a goal of the present invention to develop a method of producing microorganisms capable of producing increased levels of L-lysine by fermentation process.

SUMMARY OF THE INVENTION

An object of the present invention is to improve the fermentative yield of L-lysine thereby resulting in lower production costs.

Another object of the present invention is to provide methods of creating microorganisms of the genus Brevibacterium or of the genus Corynebacterium which have an improved L-lysine productivity and methods of producing lysine by culturing and fermenting these novel microorganisms.

As a result of various investigations to obtain mutants having improved lysine productivity in microorganisms belonging to the genus Brevibacterium or alternatively Corynebacterium, the inventors have discovered a direct correlation to a microorganism's ability to produce L-lysine and that microorganism's resistance to 4-N-(D-alanyl)-2,4-diamino-2,4-dideoxy-L-arabinose (hereinafter referred to as "pulmycin") or a derivative thereof. Examples of suitable derivatives include those shown in the following table:

EXAMPLES OF PULMYCIN DERIVATIVES

| Code No. | Structure |
|---|---|
| NK-25574 | CH$_3$CHCOHN-, NHAc, OAc, OAc, NHAc |
| NK-25575 | CH$_3$CHCOHN-, NHCOEt, OCOEt, OCOEt, NHCOEt |
| NK-25573 | CH$_3$CHCOHN-, NHCOPr(i), OCOPr(i), OCOPr(i), NHCOPr(i) |
| NK-25572 | CH$_3$CHCOHN-, NHCbz, OH, OH, NHCbz |
| NK-25576 | CH$_3$CHCOHN-, NHCbz, OAc, OAc, NHCbz |

(* shows D-form)

The correlation between L-lysine production and pulmycin resistance in microorganism has been previously unknown in the biological arts.

Pulmycin is a known antibiotic produced by a bacteria belong to the genus Bacillus. The antibiotic pulmycin and derivatives thereof useful in the present invention include those having a chemical structure similar to pulmycin and having a biological activity similar to pulmycin.

These and other objects which will become apparent during the course of the following description of exemplary embodiment which are given for illustration of the invention and are not intended to be limiting thereof.

DETAILED DESCRIPTION OF THE PREFERRED EMBODIMENTS

The L-lysine producing mutant of the present invention may be derived from a parent strain irrespective of species and strain so long as the microorganism belongs to the genus Brevibacterium or alternatively to the genus Corynebacterium provided that the strain, hereafter referred to as the "parent strain".

In a preferred embodiment the parent strain will further be characterized by having increased L-lysine productivity in addition to at least one of the properties such as resistance to S-(2-aminoethyl)-L-cysteine in the presence of L-threonine, L-homoserine auxotrophy, etc. Parent strains known to be Coryne-type L-glutamate-producing bacteria are preferred which parent strains include but are not limited to the following microorganism:

Brevibacterium divalycatum ATCC 14020
Brevibacterium flavum ATCC 14067
Brevibacterium lactofermentum ATCC 13869
Brevibacterium roseum ATCC 13825
Corynebacterium acetacidophylum ATCC 13870
Corynebacterium lilium ATCC 15990
Corynebacterium glutamicum ATCC 13032

Furthermore, strains having an improved L-lysine productivity by additionally imparting L-alanine auxotrophy, fluoropyruvic acid sensitivity, etc., to the strains having L-lysine productivity described above may also be used as the parent strain.

The term "pulmycin resistance" as used in the present invention refers to a property of a microorganism which enables such microorganism to grow in a medium containing high concentrations of pulmycin, such concentrations which would normally impede or deter the growth of the parent strain.

In addition to obtaining mutants of the present invention from parent strains which are previously known to be L-lysine producing mutants, the mutants may also be obtained by imparting pulmycin resistance to a wild strain of Coryne-type bacteria and then sequentially imparting chemical resistance or nutrient auxotrophy to thereby improve lysine productivity.

In order to impart such a pulmycin resistance to the parent strain microorganism, the parent strain is subjected to any conventional mutational treatment including but not limited to ultraviolet irradiation or a chemical treatment such as N-methyl-N'-nitro-N-nitrosoguanidine (hereinafter referred to as "NTG"), nitric acid, etc. Specific non-limiting examples are provided.

The L-lysine-producing microorganism Brevibacterium lactofermentum (AJ 12435, FERM BP-2294) was treated with 250 μg/ml of NTG at 30° C. for 30 minutes. A culture of Brevibacterium lactofermentum AJ 12435 was deposited with Fermentation Research Institute, Agency of Industrial Science and Technology (1-3, Higashi, 1-chome, Tsukuba-shi, Ibaraki-ken 305, Japan) under the deposit numbers of FERM BP 2294 on Feb. 20, 1989. Minimum nutrient plate medium (Table 1) containing 3 mg/l of pulmycin were inoculated with the treated cells exhibited a survival rate of 1%. After incubation at 30° C. for 7 days, colonies were collected for further characterization.

TABLE 1

Composition of Minimum Medium

| Component | Concentration |
|---|---|
| Glucose | 20 g/l |
| Ammonium sulfate | 10 g/l |
| $KH_2PO_4$ | 1 g/l |
| $MgSO_4.7H_2O$ | 0.4 g/l |
| $FeSO_4.7H_2O$ | 10 mg/l |
| $MnSO_4.4H_2O$ | 10 mg/l |
| Biotin | 50 μg/l |
| Thiamine hydrochloride | 100 μg/l |
| Urea | 2 g/l |
| pH | 7.0 |

The resulting colonies were tested for pulmycin resistance in order to determine the minimum inhibitory concentrations. Degree of growth was determined as follows. A medium containing yeast extract (10 g/l), peptone (10 g/l), sodium chloride (5 g/l) and agar (20 g/l) at pH 7.0 was sterilized by heating at 120° C. for 20 minutes. The agar plates were inoculated with a sterile physiological saline suspension of the selected mutant strain which was previously cultured in a bouillon slant for 24 hours. The plates were inoculated with a bacterial count of approximately $10^6$. Paper disks containing various concentrations of pulmycin were placed onto the inoculated plate and incubated at 30° C. for 48 hours. The presence of growth inhibition circles were observed and recorded.

A representative mutant strain was selected and named Brevibacterium lactofermentum AJ 12529, FERM-P-11579 FERM-BP-4073 also selected was a strain Corynebacterium which was exposed to the same mutanigizing conditions as the Brevibacterium species. Corynebacterium acetacidophylum (AJ 12415, FERM-BP-2295) was used as the parent strain and the resulting pulmycin resistant strain AJ 12530, FERM-P 11580 FERM-BP-4074 was selected for, incubated, and tested for pulmycin resistance as described above. Cultures of the microorganisms Brevibacterium lactofermentum AJ 12529, Corynebacterium acetacidophylum AJ 12415 and Corynebacterium acetacidophylum AJ 12530 were deposited with Fermentation Research Institute, Agency of Industrial Science and Technology (1-3, Higashi, 1-chome, Tsukuba-shi, Ibaraki-ken 305, Japan) under the deposit numbers of FERM BP 4073, 2295 and 4074, respectively, on Nov. 12, 1992, Feb. 20, 1989 and Nov. 12, 1992, respectively. Resistance to pulmycin with respect to the thus obtained mutant is shown in Table 2.

TABLE 2

| | Degree of Growth | | | | |
|---|---|---|---|---|---|
| | Concentration of Pulmycin | | | | |
| | (hydrochloride) | | | (mg/ml) | |
| Strain | 0 | 1 | 2 | 3.5 | 5 |
| AJ 12435 (parent) | ++ | ++ | + | − | − |
| AJ 12529 | ++ | ++ | ++ | + | + |
| AJ 12415 (parent) | ++ | ++ | + | − | − |
| AJ 12530 | ++ | ++ | + | + | − |

The degree of mutant growth set forth in Table 2, is indicated by ability of the microorganism to grow in the presence of the shown concentrations of pulmycin. The levels of growth of the parent strain are set forth followed by the levels of growth of the selected mutants. The symbols ++ and + indicate excellent and good growth, respectively, whereas the symbol− indicates no growth.

In order to effect L-lysine production with the mutants of the present invention, the mutants may be fermentatively cultured in a conventional nutrient medium containing carbon sources, nitrogen sources, inorganic salts, and if necessary further containing organic trace nutrients. No particular difficulty is involved in culturing the mutants of the present invention by standard fermentation technology.

The carbon sources used in the present invention may include standard carbon sources including carbohydrate such as glucose, molasses, etc.; organic acids such as pyruvic acid, citric acid, etc.; and alcohol such as ethanol, etc.

The nitrogen sources may include ammonium sulfate, ammonium nitrate, ammonium chloride, ammonium phosphate, ammonium hydroxide, ammonium gas, and other conventional nitrogen sources.

Organic trace nutrients include soybean protein hydroxylate, yeast extract, etc. and other conventional organism nutrient sources.

Incubation of the L-lysine producing mutants of the present invention is preferably performed under aerobic conditions at a fermentation temperature of 30 to 35° C. for a fermentation period of 40 to 100 hours.

It is preferred that the pH of the fermentation be maintained in a range of from 6.5 to 7.0 during the course of incubation. The pH of the fermentation may be adjusted using standard methods including the addition of inorganic or organic acidic or alkaline substances, urea, calcium carbonate, ammonium hydroxide, etc.

The L-lysine produced during the fermentation may be collected from the fermentation broth by standard methods which include but are not limited to ion exchange resin methods or other known methods.

By culturing the pulmycin-resistant strains as described above, the level of L-lysine production and accumulation is markedly increased as compared to the parent strain. Comparative fermentations between the parent strain and the mutants derived therefrom are described in the following examples and the data set forth in Tables 3 and 4.

The amount of L-lysine accumulated was determined by converting the amino acid into the hydrochloride which was then subjected to quantitative determination by acidic copper ninhydrin colorimetry.

EXAMPLES

Example 1

A medium containing glucose (36 g/l), ammonium chloride (20 g/l), $KH_2PO_4$ (1 g/l), $MgSO_4 \cdot 7H_2O$ (400 m/l), $FeSO_4 \cdot 7H_2O$ (10 mg/l ), $MnSO_4 \cdot 4H_2O$ (8 mg/l ), soybean protein acid hydrolysate (1 mg/l when calculated as nitrogen), thiamine hydrochloride (0.1 mg/l ) and biotin (0.3 mg/l ) was prepared. Flasks (500 ml) were charged with 20 ml each of the above described medium and subjected to sterilization by heating at 120° C. for 10 minutes, after which calcium carbonate (1 g) which had previously been subjected to dry heat sterilization was added to the medium. The culture flask were inoculated with the desired microbial strain and incubated at 31.5° C. for 48 hours in a back-and-forth shaker. The amount of L-lysine accumulated in the fermentation was quantatively determined (calculated as the hydrochloride) by acidic copper ninhydrin colorimetry, the results of which are set forth in Table 3. In all of the pulmycin-resistant strains, a remarkable increase in L-lysine accumulation was observed, as compared to the parent strain.

TABLE 3

| Amount of L-Lysine Hydrochloride Accumulated | | |
|---|---|---|
| Strain | Amount Accumulated | Yield based on Sugar (%) |
| AJ 12435 (parent) | 9.3 | 25.8 |
| AJ 12529 | 11.3 | 31.5 |
| AJ 12415 (parent) | 7.3 | 29.5 |
| AJ 12530 | 10.3 | 28.7 |

Example 2

A medium using blackstrap molasses as sugar sources and containing $KH_2PO_4$ (80 g/l), $MgSO_4 \cdot 7H_2O$ (1 g/l) and ammonium chloride (5 g/l, pH 7.0) was prepared. Flasks (500 ml) were charged with 20 ml each of the above described medium and subjected to sterilization by heating at 115° C. for 10 minutes, after which calcium carbonate (1 g) previously subjected to dry heat sterilization was added to the medium. The flasks were inoculated with the desired microbial strain and incubated at 31.5° C. for 72 hours in a back-and-forth shaker. The amount of L-lysine which accumulated in the fermentation was quantitatively determined (calculated as the hydrochloride) by acidic copper ninhydrin colorimetry the results of which are set forth in Table 4. In all of the pulmycin-resistant strain, remarkable increase in L-lysine accumulation was observed as compared to the parent strain.

TABLE 4

| Amount of L-Lysine Hydrochloride Accumulated | | |
|---|---|---|
| | Amount Accumulated (g/l) | Yield based on Sugar (%) |
| AJ 12435 (parent) | 10.4 | 25.5 |
| AJ 12529 | 23.8 | 29.8 |
| AJ 12415 (parent) | 17.3 | 21.7 |
| AJ 12530 | 21.3 | 26.6 |

The experimental results above clearly demonstrate the utility of the present invention. By practicing the present invention, it is expected that production cost of L-lysine can be greatly reduced.

Obviously, numerous modifications and variations of the present invention are possible in light of the above teachings. It is therefore to be understood that within the scope of the appended claims, the invention may be practiced otherwise than as specifically described herein.

What is claimed as new and desired to be secured by Letters Patent of the United States is:

1. A process for producing L-lysine by fermentation which comprises;
   (a) culturing a microorganism derived from a parent strain belonging to a genus selected from the group consisting of Brevibacterium and Corynebacterium, wherein said microorganism has a resistance to 4-N-(D-alanyl)-2,4-diamino-2,4-dideoxy-L-arabinose or a derivative thereof; and
   (b) collecting L-lysine from the culture media.

2. The process of claim 1, wherein said parent strain microorganism is a known L-lysine producing microorganism.

3. The process of claim 1, wherein said parent strain microorganism exhibits resistance to S-(2-aminoethyl)-L-cystein in the presence of L-threonine.

4. The process of claim 1, wherein said parent strain microorganism exhibits L-homoserine auxotrophy.

5. The process of claim 1, wherein said parent strain microorganism is a L-glutamate-producing bacteria.

6. The process of claim 5, wherein said parent strain microorganism is selected from the group consisting of Brevibacterium divalycatum ATCC 14020, Brevibacterium flavum ATCC 14067, Brevibacterium lactofermentum ATCC 13869, Brevibacterium roseum ATCC 13825, Corynebacterium acetacidophylum ATCC 13870, Corynebacterium lilium ATCC 15990, and Corynebacterium glutamicum ATCC 13032.

7. The process of claim 1, wherein said microorganism is resistant to 4-N-(D-alanyl)-2,4-diamino-2,4-dideoxy-L-arabinose or a derivative thereof at concentrations of greater than 2 mg/ml.

8. The process of claim 7, wherein said microorganism is Brevibacterium lactofermentum AJ 12529, FERM-P 11579, FERM-BP-4073.

9. The process of claim 7, wherein said microorganism is *Corynebacterium acetacidophylum* AJ 12530, FERM-P 11580, FERM-BP-4074.

10. A process for producing L-lysine by fermentation which comprises (a) mutagenizing a parent strain microorganism belonging to a genus selected from the group consisting of Brevibacterium and Corynebacterium, by exposing said parent strain to a mutagen; (b) culturing said mutagenized microorganism in the presence of 4-N-(D-alanyl)-2,4-diamino-2,4-dideoxy-L-arabinose or a derivative thereof; (c) culturing said mutagenized microorganisms having a resistance to 4-N-(D-alanyl)-2,4-diamino-2,4-dideoxy-L-arabinose or a derivative thereof; and (d) collecting L-lysine from the culture medium.

* * * * *